United States Patent [19]

Falb et al.

[11] Patent Number: 4,825,860
[45] Date of Patent: May 2, 1989

[54] DEVICE FOR SUPPLYING ANESTHETIC DISPENSING SYSTEMS

[75] Inventors: Wolfgang Falb, Krummesse; Martin Ryschka, Stockelsdorf; Carl-Friedrich Wallroth, Lübeck, all of Fed. Rep. of Germany

[73] Assignee: Draegerwerk, AG, Fed. Rep. of Germany

[21] Appl. No.: 186,691

[22] Filed: Apr. 21, 1988

Related U.S. Application Data

[63] Continuation of Ser. No. 880,719, Jul. 1, 1986, abandoned.

[30] Foreign Application Priority Data

Jul. 1, 1985 [DE] Fed. Rep. of Germany ....... 3523948

[51] Int. Cl.$^4$ .................................. A61M 16/00
[52] U.S. Cl. .................... 128/203.12; 128/204.18; 128/205.24; 206/363
[58] Field of Search ......... 128/202.27, 203.12–203.24, 128/204.18, 205.25, 205.24; 206/363; 137/583–589; 251/226–227

[56] References Cited

U.S. PATENT DOCUMENTS

| | | | |
|---|---|---|---|
| 2,720,203 | 10/1955 | Burns et al. | 128/203.12 |
| 3,162,192 | 12/1964 | Gardner | 128/203.14 |
| 3,441,020 | 4/1969 | Wortz et al. | 128/205.25 |
| 3,561,918 | 2/1971 | Ray | 206/363 X |
| 3,838,687 | 10/1974 | Mosher | 128/203.12 X |
| 4,157,092 | 6/1979 | Fare et al. | 128/202.27 |
| 4,576,157 | 3/1986 | Raghuprasad | 128/203.15 X |

FOREIGN PATENT DOCUMENTS 0882602 7/1953 Fed. Rep. of Germany ....................... 128/203.12

Primary Examiner—Edward M. Coven
Assistant Examiner—Angela D. Sykes
Attorney, Agent, or Firm—McGlew & Tuttle

[57] ABSTRACT

A device for supplying anesthetic dispensing systems with liquid anesthetics from one or more storage vessels is, for the purpose of easy exchange of different storage vessels containing different anesthetics, includes a module defining a receiving cavity which can be connected with the anesthetic dispensing system via an anesthetic infeed and can also be connected to a selected bottle or container.

8 Claims, 2 Drawing Sheets

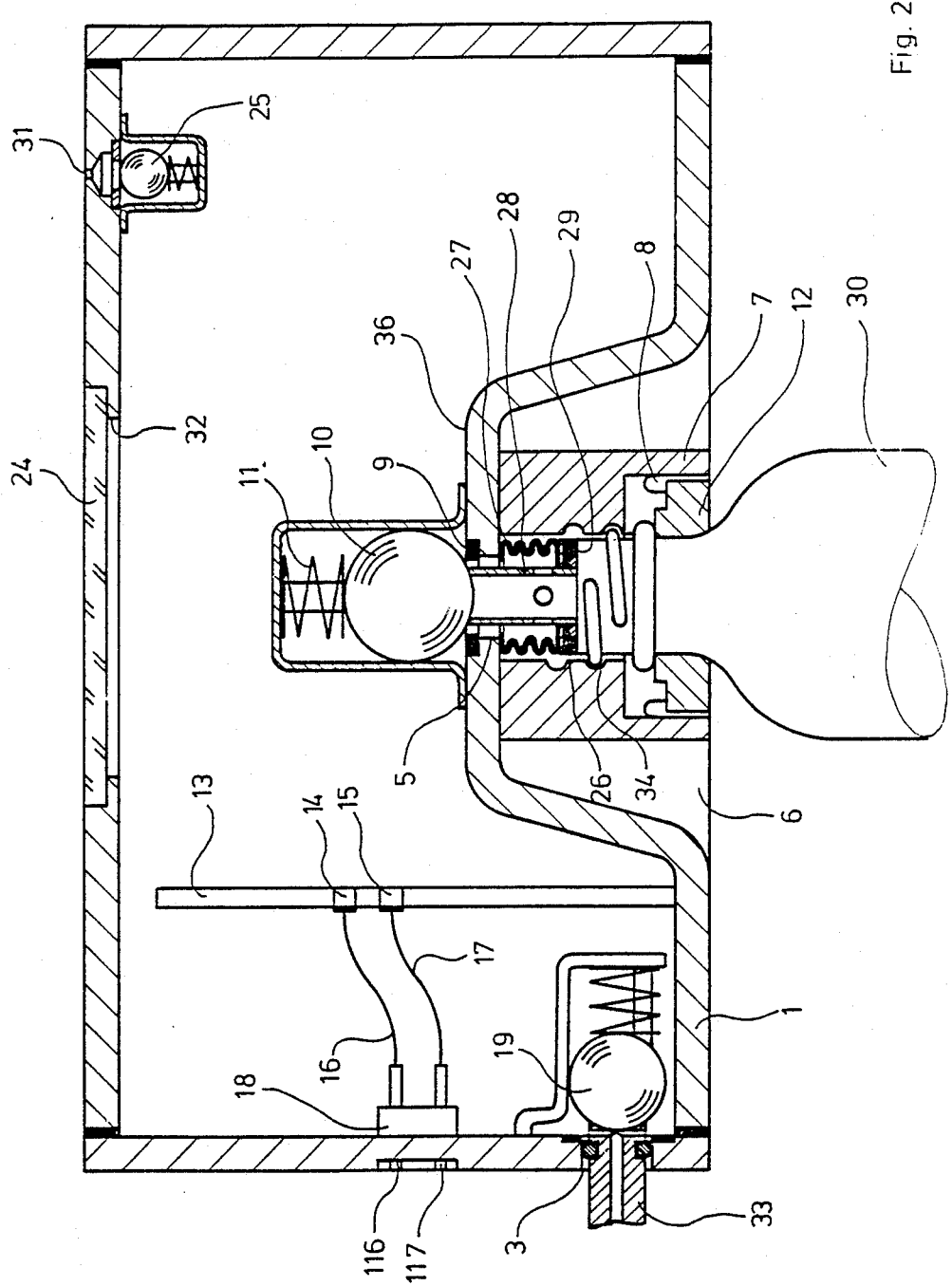

DEVICE FOR SUPPLYING ANESTHETIC DISPENSING SYSTEMS

This application is a continuation of application Ser. No. 880,719, filed July 1, 1986, now abandoned.

FIELD AND BACKGROUND OF THE INVENTION

The invention relates in general to fluid dispensers and in particular to a new and useful device for supplying anesthetic dispensing systems with liquid anesthetics from one or more storage vessels.

A similar device is described in the application No. P 34 01 923.5 which has not yet issued as a patent. The device for admixing liquid anesthetics into the respiratory gas to be supplied to the patient is indicated, which contains several anesthetic tanks filled with the respective anesthetic. Each individual anesthetic tank is connected via its own feed line to an anesthetic switching means. When changing from one anesthetic to another, the switching means connects the respective anesthetic feed line with a pump which guides the anesthetic to the anesthetic vaporizer.

Such an anesthetic pool in several anesthetic tanks to be disposed in the anesthesia apparatus requires adequate space in the anesthesia apparatus, which cannot be utilized for other purposes when only one or also two anesthetics are used, since the other tanks, though present, are not needed. The filling of the anesthetic tanks must occur directly at the anesthesia apparatus, so that an undesirably long down time of the entire apparatus must be accented, as use of the apparatus must be interrupted while it is being filled.

The leaks of anesthetic, inevitable during filling, pollute the ambient atmosphere and hence affect personnel operating the apparatus. The switching means provided for automatic switching from one anesthetic tank to another is another apparatus part requiring additional space in the anesthesia apparatus.

SUMMARY OF THE INVENTION

The invention provides a device for handling several different anesthetics which has space for only a single storge vessel, but the filling of the storage vessels can be done separately from the anesthesia apparatus. The storage vessel is in the form of a module and is connectable via the anesthetic feed line with the anesthetic dispensing system.

The advantage of the present invention is to be seen in that when changing from one anesthetic to another the vessel no longer needed can, as an independent module, be exchanged for another vessel already filled with the new anesthetic. The time required for this depends only on how quickly the connection with the anesthetic feed line can be established. This, however, is possible with the known plug connections usable therefor in so short a time that use of the anesthesia apparatus when changing vessels is interrupted for an insignificantly short time. Also it is possible to replace an empty vessel with a filled one quickly, the filling being done in areas provided therefor outside the region where anesthesia apparatus is used. Once filled, the vessel can then be transported and stored as an independent unit. The storage vessels needed in the course of an anesthesia can be filled with the respective anesthetics before or during use of the apparatus and be inserted as needed without involving a significant down time for the anesthesia apparatus. Moreover, the possibility of using different anesthetics no longer depends on the number of storage vessels installed fixed in the anesthesia apparatus. As space for only one storage vessel needs to be provided in the anesthesia apparatus, further space is not needed even when using several storage vessels.

The storage vessels may be modules provided for single use. However, it is desirable to provide a filling spout for filling the empty storage vessels from a refill vessel. To this filling spout a refill vessel, e.g. an anesthetic bottle, is connectable.

The filling spout is located preferably in a depression of the storage vessel, so that during filling from the refill vessel an air cushion can form in the surrounding of the depression inside the storage vessel. This gas volume remaining after the filling of the storage vessel can absorb volume changes of the liquid due to thermal expansion. Besides, the filling spout is protected against mechanical damage in the depression.

Appropriately the filling spout contains an uptake provided with a coding system at the refill vessel. A closure element openable in a filling direction clears the filling spout during the filling operation from the refill vessel and closes the spout after termination of the filling operation.

For monitoring the filled level inside the storage tank there serves, in further development of the invention, a level indicator consisting for example of a communicating tube arranged on the back of the storage vessel. Thereby the filling level of the vessel in the installed state can be checked easily.

Futhermore, there may be used as level indicator also another known level indicator which operates for example on the principle of thermal conductivity, length of path movement via a float, or capacitance measurement. The known level indicators are connected via suitable connecting elements to an evaluating and display unit contained in the anesthetic dispensing system.

In further development of the invention the storage vessel is provided with a marking which enables the user to check the anesthesia apparatus which anesthetic is being supplied to the anesthetic dispensing system through the inserted storage vessel.

When connecting the storage vessel to the tap, the respective opening in the storage vessel is opened appropriately by a seal element allowing the supply of anesthetic.

To perform the connection of the storage vessel to the anesthetic dispensing system safely and reliably, a guide is provided which excludes making a connection of a different kind.

This is accomplished in an especially simple manner in that the guide consists of rails converging at an acute angle in the direction of the anesthetic dispensing system. With adapted acute-angle convergence of the respective base surfaces of the storage vessel a connection ready for operation to the anesthetic dispensing system is established at correct insertion.

For easy visual control of the filled state of the storage vessel during filling it is provided that at a suitable point a viewing window is applied.

To compensate the volume of anesthetic removed during use of the vessel, a vacuum valve is provided, through which ambient air can enter the interior of the storage vessel.

Accordingly it is an object of the invention to provide a device for supplying anesthetic dispensing systems with liquid anesthetics comprisgna storage vessel having an interior anesthetic receiving chamber with an anesthetic infeed connection.

A further object of the invention is to provide a device for supplying anesthetic dispensing systems which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

FIG. 2 is a section through the storage vessel line A—A with attached refill vessel.

DESCRIPTION OF THE PREFERRED EMBODIMENTS

Figure 1:
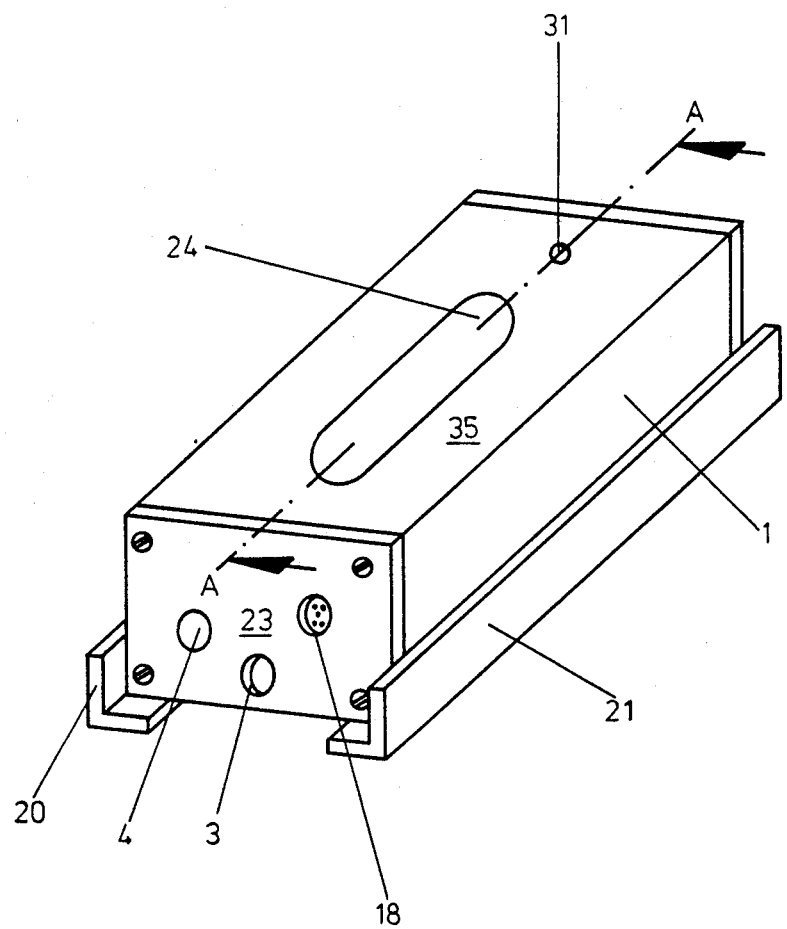
FIG. 1 is a perspective view of the storage vessel.

Referring to the drawings in particular the invention embodied therein comprises a device for supplying anesthetic dispensing systems with liquid anesthetics from one or more storage vessels which comprises a storage vessel 1 in the form of a module which is connectable with an anesthetic dispenser through an anesthetic infeed connection 3. The device also includes a filling spout 5 for connecting it to a refill vessel or pressure bottle 30.

The storage vessel 1 shown in FIG. 1 has at one end face 23 an anesthetic infeed 3 as well as a marking 4 specific for the respective anesthetic. Next to it is a connection 18 for supplying the electric signals from the level indicator 13 to the anesthesia apparatus (not shown). At the top 35 a viewing window 24 is applied via an opening 32 as well as an opening 31 to the vacuum valve 25. The storage vessel 1 is guided over the rails 20, 21.

In the section through storage vessel 1 shown in FIG. 2, the uptake 7 is disposed in the depression 6 which the filling spout 5 contains. The uptake 7 is designed so that the refill vessel 30, for example, in the form of an anesthetic bottle, can be screwed into its thread 34 into the respective cutouts of uptake 7. As the bottle 30 is being screwed in, its end face 29 strikes against the flat packing 26, which is held by a metal bellows 27. The metal bellows 27 ensures secure sealing of the anesthetic bottle against the flat packing 26 before the tube 28, due to further screwing in of the anesthetic bottle 30 against the force of metal bellows 27, lifts the ball 10 off its seat 9 counter to spring 11 and connects the interior of the storage vessel 1 with the anesthetic bottle, 30. When the anesthetic bottle 30 is screwed out of the uptake 7, the filling spout 5 is closed off from the surrounding. To ensure foolproof connecting of the various anesthetic bottles 30, the uptake 7 has a coding system 8 specific for the respective anesthetic. Into it engages the coding collar 12 of bottle 30.

To connect the anesthetic infeed 3 to the respective dispensing nipple 33 of the anesthetic dispensing system (not shown in the figure), a valve 19 is actuated, whose mode of operation is similar to that of the closure elements 9 and 10.

For indication of the respective filling level in the storage vessel 1 a level indicator 13 is applied. It has two electrodes 14,15 which by leads 16,17 are wired to the connection 18. Connection 18 is connectable with the anesthetic dispensing system (not shown) via plug contacts 116, 117.

For filling the storage vessel 1, the anesthetic bottle 30, for example, is screwed in the uptake 7 and the storage vessel 1 tilted in such a way that its side wall with the viewing window 24 is directed downward while its side wall with the depression 6 is directed upward. Through the opened closure elments 9 and 10, the anesthetic liquid flows from bottle 30 into vessel 1, and the air contained therein can escape into bottle 30 until the filled level has reached the dip 36. Now the filling process can be terminated, the storage vessel tilted back into its starting position, and the anesthetic bottle 30 screwed out of the uptake 7. For connection to the anesthetic dispensing system of the anesthesia apparatus the storage vessel 1 is now connected via the guide rails 20, 21 to the dispensing nipple 33, the valve 19 being opened and also the connection 18 being coupled.

While a specific embodiment of the invention has been shown and described in detail to illustrate the application of the principles of the invention, it will be understood that the invention may be embodied otherwise without departing from such principles.

What is claimed is:

1. A device for supplying anesthetic dispensing systems with liquid anesthetics using one or more storage vessels, comprising a gastight closed storage vessel module having a wall with an anesthetic infeed connection and having an interior chamber into which the anesthetic may flow, a displaceable infeed valve member closing said infeed, means biasing said infeed valve member to a position closing said infeed, said valve member being displaceable against said biasing by insertion of the nipple in said infeed connection, wherein said storage vessel includes a wall with a depression forming a recess on its wall extending into the interior of the vessel, a filling spout in said depression, including a guide on which said vessel is movable, said vessel wall having said infeed connection being arranged at an end of said vessel and said vessel being movable along said guide so as to connect it to an anesthetic dispensing system, and wherein said guide comprises two spaced apart rails converging at an acute angle in the direction of the anesthetic dispensing system.

2. A device for supplying anesthetic dispensing systems which have an anesthetic infeed connection nipple with liquid anesthetics using at least one storage vessel, comprising a gastight closed storage vessel module having a wall with an anesthetic infeed connection and having an interior chamber into which the anethetic may flow from said connection, a displaceable infeed valve member closing said infeed connection, means biasing said valve member to a position closing said infeed connection, said valve member being displaceable against said biasing by insertion of the nipple in said infeed connection, a filling spout connected into said storage vessel having an anesthetic container filling spout connected into said storage vessel and having an anesthetic container spout receiving fitting into which an anesthetic bottle is engageable.

3. A device according to claim 2, wherein said storage vessel includes a wall with a depression forming a recess on its wall extending into the interior of the vessel, said depression containing said filling spout.

4. A device according to claim 2, including a level indicator associated with said storage vessel.

5. A device according to claim 2, wherein said storage vessel includes a mark.

6. A device according to claim 2, including a viewing window defined in a wall of said storage vessel.

7. A device according to claim 2, wherein said anesthetic infeed connection includes a seal element between said infeed connection and said connection and nipple allowing the supply of anesthetic.

8. A device according to claim 2, including a vacuum valve mounted in the wall of said vessel between the exterior and the interior thereof said valve, being openable to admit air when the anesthetic is being drained from said interior chamber.

* * * * *